United States Patent [19]

Maeda et al.

[11] Patent Number: 5,399,550

[45] Date of Patent: * Mar. 21, 1995

[54] PHYSIOLOGICALLY ACTIVE SUBSTANCE DERIVED OR MALT AND PROCESS FOR THE PRODUCTION THEREOF

[75] Inventors: Yuji Maeda, Chiba; Takayoshi Fujii; Masanori Ikuzawa, both of Tokyo; Kenichi Matsunaga, Saitama; Tamotsu Kanoh, Chiba; Shigeaki Muto, Tokyo, all of Japan

[73] Assignee: Kureha Chemical Industry Co., Ltd., Tokyo, Japan

[ * ] Notice: The portion of the term of this patent subsequent to May 17, 2011 has been disclaimed.

[21] Appl. No.: 947,787

[22] Filed: Sep. 18, 1992

Related U.S. Application Data

[62] Division of Ser. No. 755,834, Sep. 6, 1991, Pat. No. 5,312,809, which is a division of Ser. No. 539,850, Jun. 18, 1990, abandoned.

[30] Foreign Application Priority Data

Jun. 28, 1989 [JP] Japan ................................ 1-166412

[51] Int. Cl.$^6$ ..................... A01N 37/18; A61K 37/00; A61K 37/10
[52] U.S. Cl. ........................................... 514/2; 514/8; 514/18; 530/372; 530/373; 426/44
[58] Field of Search ................. 514/2, 8, 18; 530/372, 530/373; 426/44

[56] References Cited

PUBLICATIONS

Ivanov et al. CA vol. 101: No. 89214x (1984).

*Primary Examiner*—Robert J. Hill, Jr.
*Assistant Examiner*—Sheela J. Huff
*Attorney, Agent, or Firm*—Burgess, Ryan & Wayne

[57] ABSTRACT

A multi-functional physiologically active substance can be obtained from the residue of saccharified malt which has been worthless other than feed for cattle. The isolation of the active substance is performed by an extraction of the residue with water or an aqueous solvent and removal of a low molecular weight fraction from the extract.

2 Claims, 4 Drawing Sheets

PHYSIOLOGICALLY ACTIVE SUBSTANCE DERIVED OR MALT AND PROCESS FOR THE PRODUCTION THEREOF

CROSS REFERENCES TO RELATED APPLICATIONS

This application is a divisional of application Ser. No. 07/755,834, filed Sep. 6, 1991, now U.S. Pat. No. 5,312,809, which is a Divisional of application Ser. No. 07/539,850, filed Jun. 18, 1990, now abandoned.

BACKGROUND OF THE INVENTION

1. Field of the Invention

This invention relates to a physiologically active substance extracted from the residue of saccharified malt and the process for the production thereof. "Physiologically active" means, for example, the inhibition of platelets aggregation, prevention of death due to acute pulmonary embolism, improvement of erythrocyte transformation, analgesic activity, anti-nephropathic action, radiation exposure protection activity, hypotensive activity, and hypoglycemic activity.

2. Description of the Prior Art

Few efforts have been known to extract and produce a useful substance from the residue of saccharified malt. For example, Japanese Laid-Open Application No. 129776 (1976) describes an extraction of a solid nutritious protein from brewed cereals such as residue of malt saccharification. However, no attempts have been known to obtain a physiologically active polymer from the waste of saccharified malt.

SUMMARY OF THE INVENTION

The present inventors have been searching for substances useful for the maintenance of human health from unused resources employed for industrial purposes. Unexpectedly, a physiologically active polymer which exhibits various useful properties for the maintenance of human health including inhibition of platelet aggregation and improvement in the transformation of erythrocytes was isolated by an extraction of residue of malt saccharification with water and accomplished the present invention. Therefore, the main purpose of the present invention is to provide a physiologically active substance from the filtered residue of a saccharified malt, by an extraction with water or an aqueous solvent, and removal of a low molecular weight fraction, and the procedure for the production thereof. Other purposes of the present invention will become apparent by the following description.

DETAILED DESCRIPTION OF THE PREFERRED EMBODIMENTS

The physiologically active substance of the present invention obtained from the residue of saccharified malt can be defined by the following properties:

(i) Molecular weight of approximately 2,000 or more.
(ii) Infrared absorption (IR) spectrum having peaks at 3,600–3,200 $cm^{-1}$ and 1,700–1,600 $cm^{-1}$.
(iii) Proton nuclear magnetic resonance (NMR) spectrum having peaks at 0.5–6.0 ppm and 6.0–8.5 ppm.
(iv) Ultraviolet absorption (UV) spectrum having peaks at 200–250 nm and 250–350 nm.
(v) Positive to the phenol sulfuric acid color reaction.
(vi) Positive to the copper-Folin color reaction.

The substance of the present invention can be produced by the following procedure.

Extraction of a filtered residue prepared by saccharification of malt with water or an aqueous solvent, and removal of a low molecular weight fraction to isolate the desired fraction.

The malt of the present invention is prepared by germinating the grains including gramineous crops. These grains include e.g. barley, wheat, rye, oats, naked barley and corn. The grains are pulverized and saccharified in warm water, and starches may be added if necessary. The saccharified mixture is filtered and the residue or filter cake is used for the raw material of the present invention. The residue has been used for cattle feed and the filtrate or wort is used for the production of beer.

The above mentioned filtered residue is then extracted with water or an aqueous solvent. Water includes preferably hot, warm and 0.02–2.0N warm alkaline aqueous solution and the aqueous solvents include hydrophilic organic solvents such as methanol, ethanol and acetone or their aqueous mixture. The extraction is performed by the addition of 10–1,000,000 weight parts of water or the aqueous solvent to 100 weight parts of dried or wet filter cake, and for a few hours to overnight. Stirring, ultrasonication or an addition of a surface active agent may be used for efficient extraction. The extraction is performed generally at temperatures of 10°–150° C., preferably at 40°–120° C., and more preferably at 60°–100° C. When an alkaline solution is used for the extraction, the resulted extract is neutralized and the formed precipitates are filtered, then a low molecular weight fraction of less than 2,000 is separated from the obtained supernatant. The extraction with an 0.1–1.0N alkaline solution provides superior extraction rate with higher water solubility of the extract than that with water without affecting the properties of extract. The extract then may be made pH 4.0 to precipitate a protein. The obtained supernatant is further neutralized to pH 7.0 to remove precipitates. A low molecular weight fraction in the supernatant is removed by various methods such as dialysis, salting out, ultrafiltration, reverse osmosis, gel filtration, or precipitation by the addition of an organic solvent to give the physiologically active fraction of the present invention. The obtained fraction can be used as it is, or may be processed before use such as condensation, lyophilization and spray drying.

The substance or extract of the present invention has the following properties:

(i) Molecular weight of approximately 2,000 or more.
(ii) Infrared absorption spectrum having peaks at 3,600–3,200 $cm^{-1}$ and 1,700–1,600 $cm^{-1}$.
(iii) Proton nuclear magnetic resonance spectrum having peaks at 0.5–6.0 ppm and 6.0–8.5 ppm.
(iv) Ultraviolet absorption spectrum having peaks at 200–250 nm and 250–350 nm.
(v) Positive to the phenol sulfuric acid color reaction.
(vi) Positive to the copper-Folin color reaction.

The physiologically active substance of the present invention showed no acute toxicity in oral administration in mice as shown in the following Example 3. The physiological activities of the substance were investigated and confirmed by the following examples of 4-12 exhibiting such as the inhibition of platelets aggregation, prevention of death due to acute pulmonary embolism, improvement of erythrocyte transformation, analgesic activity, anti-nephropathic activity, radiation exposure protecting activity, hypotensive activity, and hypoglycemic activity. These properties are particularly useful for the geriatric diseases of various systems such as central nervous system, circulatory system, urinary system, an metabolic system which are expected to become more important in the future. The substance is safe and very useful for the maintenance of human health and will be one of the awaited medicines.

The physiologically active substance of the present invention can be used as an anti-thrombotic agent, anti-ischemic agent, analgesic, anti-nephrophathic agent, radiation exposure protecting agent, anti-hypertensive agent, and anti-diabetic agent for the prevention and treatment of above mentioned diseases in the forms of medicines or foods and drinks. The substance can be orally administered at 0.01-10,000 mg/kg daily in several divided forms such as tablets, powders, granules, or capsules. The substance can be used as foods and drinks and can be taken at 0.01-10,000 mg/kg daily as it is or as an additive for the processed cakes such as biscuits, crackers, snacks, rice cakes, chocolates, cocoas, chewing gums, candies, western, Japanese and Chinese cakes, doughnuts, pizzas, crepes, chilled desserts, breads and buns, and noodles, macaronies, pickles, tofu (bean curds), processed meats such as hams and sausages, milk products such as butters, cheeses, yogurts, milk and ice creams, and margarines, hamburgers and seasonings. The substance can be added to drinks such as carbonated water, soda pops, ciders, fruits juices, pulverized fruit juices, mineral water, soya milk, coffee, tea, green tea., toasted tea, and oolong tea.

The present invention is further explained by the following examples, but these examples are illustrated to exemplify the present invention and the scope of the present invention is not restricted by these examples.

EXAMPLE 1

Ten kg of barley were germinated, mixed with proper amount of starch and saccharified by a conventional method. The saccharified mixture was filtered and the filtered residue was dried.

One hundred gram of the saccharified residue was added to four L of 0.5N NaOH and extracted for three hours under boiling. The extract was made pH 4.0 with 1N HCl and allowed to stand. The formed precipitates were separated by centrifugation at 6,000 rpm for 30 minutes. The obtained supernatant was neutralized to pH 7.0 with 1N NaOH and centrifuged again at 6,000 rpm for 30 minutes. The obtained supernatant was condensed under reduced pressure, dialyzed against running water (Visking cellulose) and lyophilized to give 23 g of the dried extract.

Figure 1:
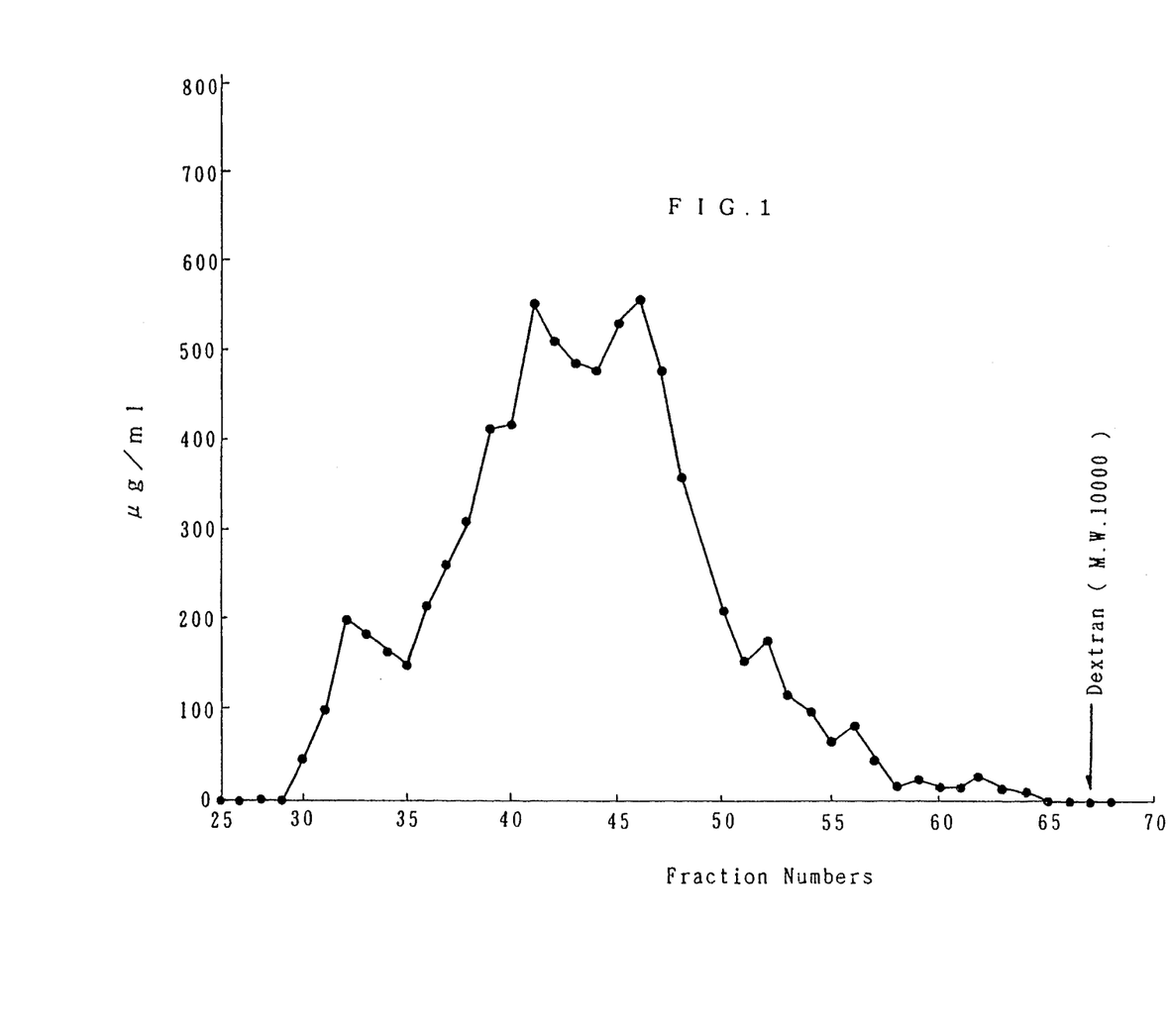
FIG. 1 shows a chromatogram of the dried extract explained in example 1.
Figure 2:
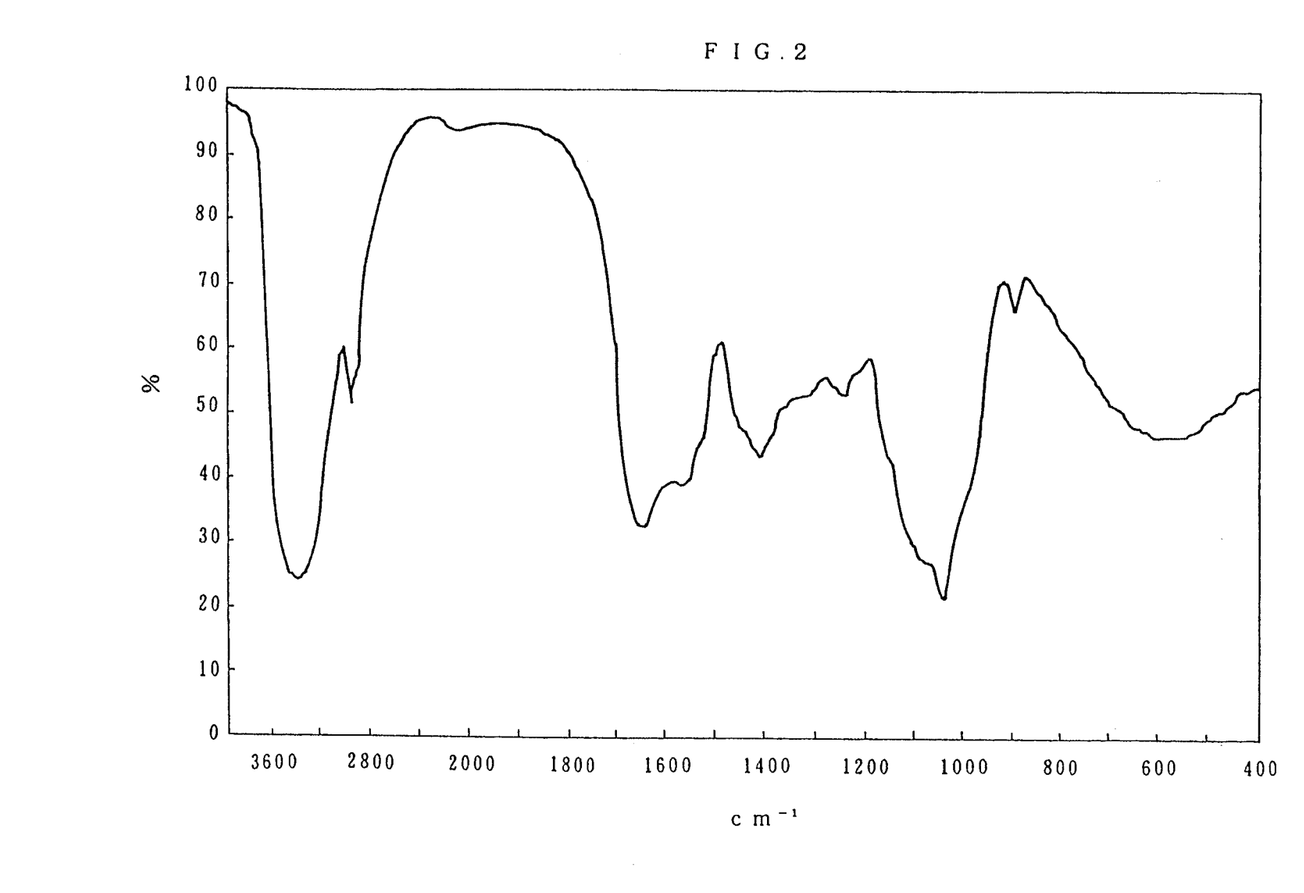
FIG. 2, 3 and 4 show an infrared absorption spectrum, a nuclear magnetic resonance spectrum and ultraviolet and visible absorption spectrum of the dried extract, respectively.
Figure 3:
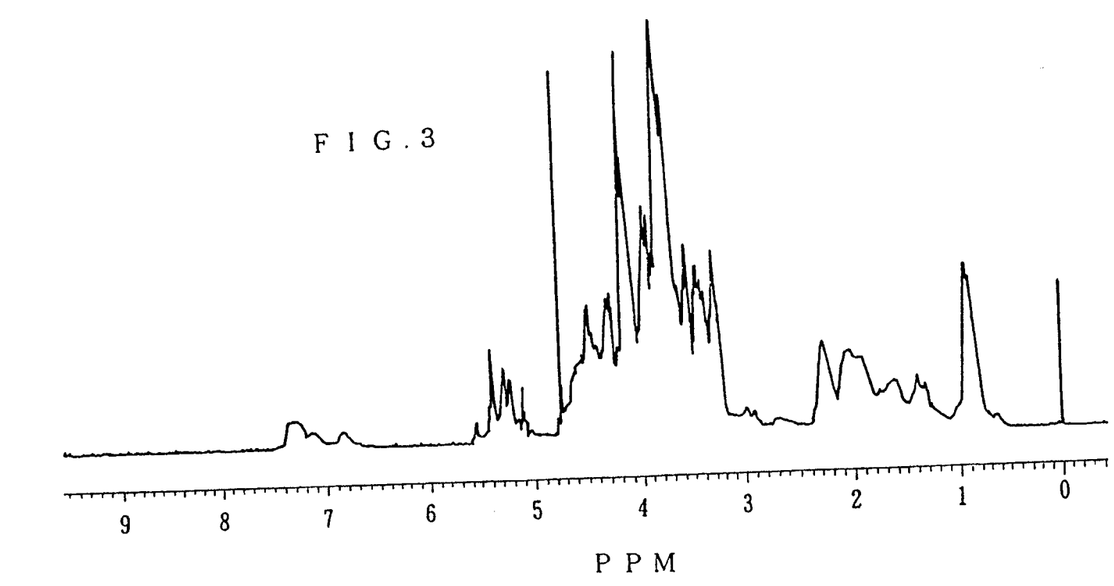
Figure 4:
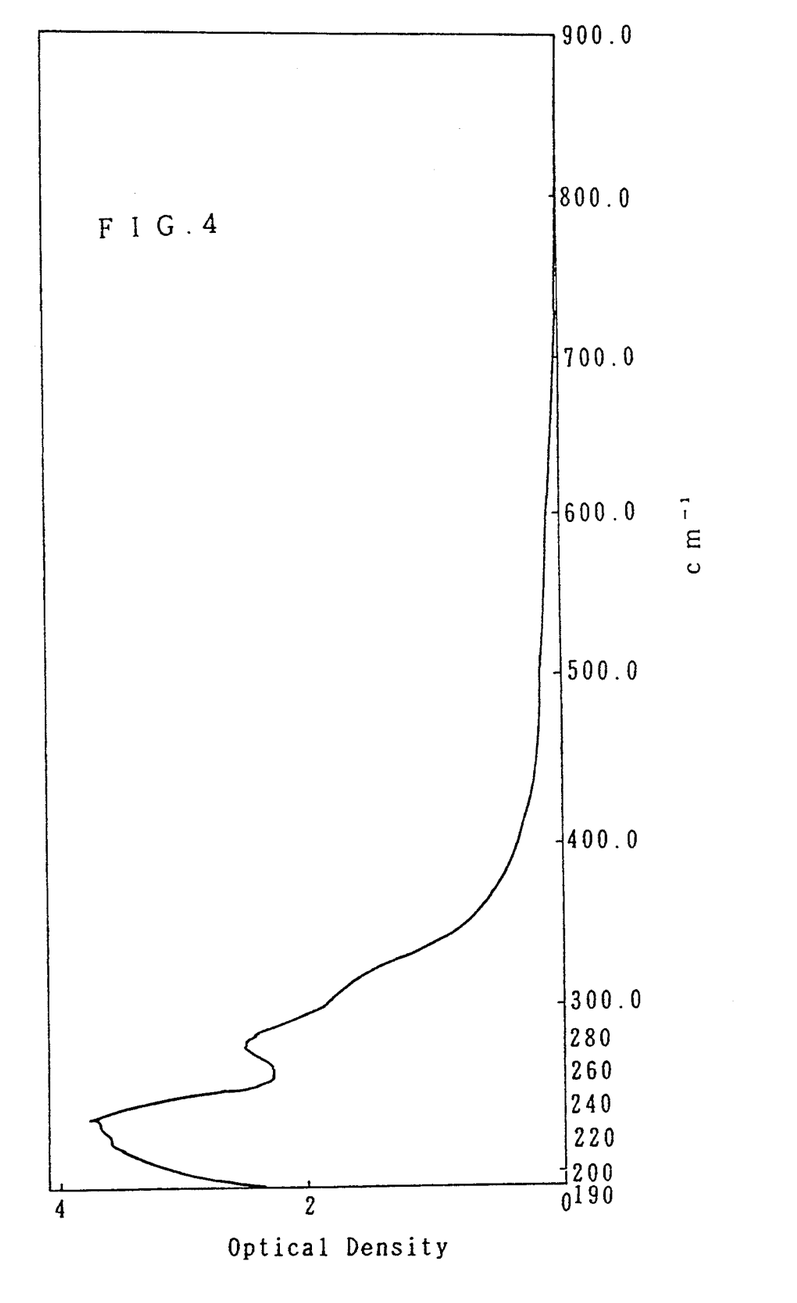

The obtained dried extract showed weight-average molecular weight of 209,000 by GPC-Lalls method. One example of a gel chromatogram of the dried extract is shown in FIG. 1 [packing material: Cellulofine GLC-2000-C, column: $\phi$2.5 cm×height 45 cm, fractionation: three ml/one fraction, detection method: color reaction with phenol sulfuric acid (490 nm), sample: injection by 30 mg/3 ml]. FIG. 1 shows the separation of a fraction of molecular weight of 10,000 or less. FIG. 2 shows an IR spectrum of the substance determined with KBr tablet by the IR spectrophotometer type A202 [Japan Spectroscopic Co., Ltd. (JASCO)]. Absorption peaks at 3,600-3,200 $cm^{-1}$ and 1,700-1,600 $cm^{-1}$ were observed. FIG. 3 shows a proton nuclear magnetic resonance (PMR) spectrum was determined with an internal standard of DSS by JMN-GSX type 500 spectrometer [Nihon Denshi Ltd. (JEOL)] at 500 MHz, revealing peaks at 0.5-6.0 ppm and 6.0-8.5 ppm. FIG. 4 shows UV and visible absorption spectra of the fraction with peaks at 2090-250 nm and 250-350 nm determined by Multipurpose Recording Spectrophotometer MPS-2000 (Shimadzu Seisakusho Ltd.). These Fig. of chromatogram and spectra represent examples of the properties of the dried extract of the present invention, and the scope of dried extract the present invention is not defined by these Fig.

The dried extract showed positive to phenol sulfuric acid color reaction revealing the presence of sugars. The composition of the sugars were analyzed after acidic hydrolysis by liquid chromatography LC-6A (Shimadzu Seisakusho Ltd.) and sugars such as arabinose, xylose, glucose and galactose were detected and confirmed. The copper-Folin color reaction was also positive indicating the presence of a protein. The contained amino acids in the protein were analyzed after acid hydrolysis by Hitachi 835 (Hitachi Ltd.) amino acid analyzer end common acidic amino acids, basic amino acids and hydrophobic amino acids were detected and confirmed.

EXAMPLE 2

Malts of wheat, rye, oats and naked barley were treated similar manner to Example 1 and resulted dried extracts, respectively. The physicochomical properties of the dried extracts were similar to those of extract of barley malt as shown in Table 1.

TABLE 1

| | Resource of extract of malt residue | | | | |
|---|---|---|---|---|---|
| Item | Barley | Wheat | Naked barley | Rye | Oats |
| Average M.W. (10,000) | 20.9 | 20.5 | 22.1 | 21.8 | 10.8 |
| Solubility in water | Freely soluble | Freely soluble | Freely soluble | Freely soluble | Freely soluble |
| Qualitative test of sugars (phenol sulfuric acid method) | positive | positive | positive | positive | positive |
| Qualitative test of peptides (Copper-Folin method) | positive | positive | positive | positive | positive |
| IR spectra 3,600-3,200 $cm^{-1}$ 1,700-1,600 $cm^{-1}$ | positive | positive | positive | positive | positive |
| NMR spectra 0.5-6.0 ppm 6.0-8.5 ppm | positive | positive | positive | positive | positive |
| UV absorption spectra 200-250 nm 250-350 nm | positive | positive | positive | positive | positive |

EXAMPLE 3

The safety of the extracts of the present invention derived of malts was tested by the method shown below.

Each of ten ICR mice (male, five weeks old) were enrolled in the study. Each of the dried extracts obtained by Examples 1 and 2, 5 g each, were dissolved in 10 ml of distilled water and orally administered by gavage at five g/kg and observed for 14 days. No dead mouse was found. The mice were sacrificed and their blood were drawn. No abnormal result was found in general blood test, blood biochemistry an pathological tests. An excellent safety of the substance was found in those acute toxicity tests.

The following examples 4–12 show the physiological activities of the dried extracts derived from malt obtained by the present invention.

EXAMPLE 4

Fresh blood was drawn by citrate added syringe from nine weeks old female Donryu rats according to the method of G. V. R. Born [Nature, 194, 927 1962] and PRP (platelet rich plasma) was obtained by centrifugation. Dried extracts obtained according to Examples 1 and 2 were added, respectively, to the PRP at 2.5 mg/ml and 50 μM of adenosine-5′-diphosphate (ADP) was added as a platelet aggregation stimulant to investigate the inhibitory activity on platelet aggregation. The control group used PRP without containing the extract.

The determination of platelet aggregation was performed by measuring the transparency of PRP using an aggrecometer (Biodata Corp.). The inhibitory rate, I, of the extract was calculated by the following equation.

$$I = \left[ 1 - \frac{\text{Change of transparency obtained by the extract}}{\text{Change of transparency in the control group}} \right] \times 100 \, (\%)$$

[No. of animals of each group (hereinafter abbreviated as $n$) = 6]

The results are shown in Table 2, revealing the excellent inhibitory activity on platelet aggregation. The results also indicate that the extract of the present invention can be applied for the prevention and treatment or thrombus formation due to its inhibitory activity, I, against platelet aggregation.

TABLE 2

| Resource of extract of malt residue | Inhibitory rate of platelet aggregation, I |
|---|---|
| Barley | ++ |
| Wheat | + |
| Naked barley | + |
| Rye | ++ |
| Oats | ++ |

The inhibitory rates, I, in the above Table 2 are classified by the following grades:

| | | |
|---|---|---|
| −; | 0 ≦ I < | 20(%) |
| +; | 20(%) ≦ I < | 30(%) |
| ++; | 30(%) ≦ I ≦ | 100(%) |

EXAMPLE 5

On thousand mg of the dried extract obtained by Example 1 or 2 was dissolved in 20 ml of distilled water and orally administered by gavage to four weeks old male ICR mice according to the method of Narday et al. at a rate of 1,000 mg/kg. After three hours, 400 mg/kg of ADP was administered to the mice in tail vein in three seconds and the mice were observed for 10 minutes to obtain the death rate for the investigation of the preventive effect against death due to acute pulmonary embolism. The control group was administered 20 ml/kg of distilled water instead of the extract. The results are shown Table 3 revealing an excellent preventive effects against death due to acute pulmonary embolism.

The results also indicate that the extract of the present invention can be applied for the prevention and treatment of thrombus formation due to its preventive activity against death caused by acute pulmonary embolism, I.

TABLE 3

| Resource of extract of malt residue | Inhibitory rate of death due to acute pulmonary embolism, I |
|---|---|
| Barley | ++ |
| Wheat | + |
| Naked barley | + |
| Rye | + |
| Oats | ++ |

The inhibitory rates, I, in the above Table 3 are classified by the following grades:

| | | |
|---|---|---|
| −; | 0 ≦ I < | 20(%) |
| +; | 10(%) ≦ I < | 30(%) |
| ++; | 30(%) ≦ I ≦ | 100(%) |

The inhibitory rate of death due to acute pulmonary embolism, I, is calculated by the following equation.

$$I = \left[ I - \frac{\text{Death rate in the administered group of the extract}}{\text{Death rate in the control group}} \right] \times 100 \, (\%)$$

EXAMPLE 6

One thousand mg of the dried extract obtained by Example 1 or 2 was dissolved in 20 ml of distilled water and orally administered by gavage to eight weeks old female Donryu rats according to the method of Furlow et al. [Science. 187, 658 (1975)] at a rate of 1,000 mg/kg. After 30 minutes, 20 mg/kg of arachidonic acid was administered to the rats intra-arterially directing toward the brain. The rats were observed to obtain the death rate for the investigation of the preventive effect against death due to thrombus. The control group was administered 20 ml/kg or distilled water instead of the extract. The results are shown in Table 4 revealing an excellent preventive effects against death due to thrombus.

The results also indicate that the extract of the present invention can be applied for the prevention and treatment of ischemia due to its preventive activity against death caused by thrombus, I.

TABLE 4

| Resource of extract of malt residue | Inhibitory rate of death due to thrombus, I |
|---|---|
| Barley | + |
| Wheat | ++ |
| Naked barley | + |
| Rye | + |
| Oats | + |

The inhibitory rates, I, in the above Table 4 are classified by the following grades:

| | | |
|---|---|---|
| —; | $0 \leq I <$ | $10(\%)$ |
| +; | $10(\%) \leq I <$ | $30(\%)$ |
| ++; | $30(\%) \leq I \leq$ | $100(\%)$ |

The inhibitory rate or death, I, due to thrombus is calculated by the following equation.

$$I = \left[ 1 - \frac{\text{Death rate in the administered group of the extract}}{\text{Death rate in the control group}} \right] \times 100 \ (\%)$$

$(n = 10)$

EXAMPLE 7

One thousand mg of the dried extract obtained by Example 1 or 2 was dissolved in one ml of distilled water and orally administered by gavage to 10 weeks old female Donryu rats according to the method of Otomatsu et al. at a rate of 1,000 mg/kg. After three hours, the blood was drawn from ventral aorta and added to 10 fold physiological saline solution. The mixture was stirred by Termo-mixer and hemolyzed and centrifugated at 1,500 rpm for five minutes. The content of hemoglobin in the obtained supernatant was determined by an absorption 540 nm.

The rate of hemolysis was calculated on the base hemolysis rate of 100 obtained by the addition of distilled water and investigated the improvement of transformation of erythrocytes by the substance of the present invention. The control group was administered one ml/kg of distilled water instead of the extract.

The results are shown in Table 5 revealing an excellent effect of improvement in the transformation of erythrocytes. The results also indicate that the extract of the present invention can be applied for the prevention and treatment of ischemia due to its activity on the improvement of transformation or erythrocytes, P.

TABLE 5

| Resource of extract of malt residue | Improved rate on the transformation of erythrocyte, P |
|---|---|
| Barley | ++ |
| Wheat | + |
| Naked barley | ++ |
| Rye | ++ |
| Oats | + |

The improved rates, P, in the above Table 5 are classified by the following grades:

| | | |
|---|---|---|
| —; | $0 \leq P <$ | $10(\%)$ |
| +; | $10(\%) \leq P <$ | $30(\%)$ |
| ++; | $30(\%) \leq P \leq$ | $100(\%)$ |

The improved rate of erythrocyte transformation, P, is calculated by the following equation.

$$P = \left[ 1 - \frac{\text{Hemolytic rate in the administered group of the extract}}{\text{Hemolytic rate in the control group}} \right] \times 100 \ (\%)$$

$(n = 6)$

EXAMPLE 8

One thousand mg of the dried extract obtained by Example 1 or 2 was dissolved in 10 ml of distilled water and orally administered by gavage to six weeks old female ICR mice according to the method described in Fundamental Course of Medicine, vol. 6, Evaluation of Drug Efficacy (1) Pharmacological Tests (Part 1) p. 283. Antipyretics Analgesic, Pub. by Chijin Shokan (1971), at a rate of 1,000 mg/kg. After 30 minutes, 0.1 ml/10 g of body weight of 2.0% acetic acid solution was intraperitoneally administered. After 10 minutes, the number of writhing was counted for 10 minutes to evaluate the analgesic effect of the extract. The control group was administered 10 ml/kg of distilled water instead of the extract.

The results are shown in Table 6 revealing an excellent analgesic effect of the substance of the present invention. The results also indicate that the extract can be applied for the diseases and symptoms which require the relief of pain.

TABLE 6

| Resource of extract of malt residue | Analgesic effect, I |
|---|---|
| Barley | + |
| Wheat | + |
| Naked barley | + |
| Rye | + |
| Oats | ++ |

The rates of activity, I, in the above Table 6 are classified by the following grades:

| | | |
|---|---|---|
| —; | $0 \leq I <$ | $10(\%)$ |
| +; | $10(\%) \leq I <$ | $30(\%)$ |
| ++; | $30(\%) \leq I \leq$ | $100(\%)$ |

The rate of analgesic effect, I, is calculated by the following equation.

$$I = \left[ 1 - \frac{\text{No. of writhing in administered group of the extract}}{\text{No. of the writhing in the control group}} \right] \times 100 \ (\%)$$

$(n = 10)$

EXAMPLE 9

Eight weeks old female Wistar rats were subcutaneously administered 10 mg/kg of an aminonucleoside for consecutive days to induce nephrosis. One thousand mg of the dried extract obtained by Example 1 or 2 was dissolved in 20 ml of distilled water and orally administered by gavage from five days before the administration of the aminonucleoside for consecutive 14 days according to the method of Caulfied et al. Urinary protein on the final day of the extract administration was determined to investigate the anti-nephrotic effect. The control group was administered 20 ml/kg of distilled water instead of the extract.

The results are shown in Table 7 revealing an excellent decrease of urinary protein concentration. The results also indicate that the extract can be widely applied for the prevention and treatment of nephropathy.

TABLE 7

| Resource of extract of malt residue | Inhibitory rate of urinary protein, I |
| --- | --- |
| Barley | ++ |
| Wheat | ++ |
| Naked barley | + |
| Rye | ++ |
| Oats | ++ |

The inhibitory rates, I, in the above Table 7 are classified by the following grades:

| | | |
| --- | --- | --- |
| —; | $0 \leq I <$ | $10(\%)$ |
| +; | $10(\%) \leq I <$ | $30(\%)$ |
| ++; | $30(\%) \leq I \leq$ | $100(\%)$ |

The inhibitory rate of urinary protein, I, is calculated by the following equation.

$$I = \left[ 1 - \frac{\text{Amount of urinary protein in the administered group of the extract}}{\text{Amount of urinary protein in the control group}} \right] \times 100 \, (\%)$$

$(n = 6)$

EXAMPLE 10

Eight weeks old male C3H/HeJ mice were systematically irradiated (3 Gy) under non-restraint condition. One thousand mg of the dried extract obtained by Example 1 or 2 was dissolved in 10 ml or distilled water and orally administered from the next day of the irradiation for consecutive days. After 12th day of the irradiation, blood was drawn from ophthalmic vein under ether anesthesia and leukocyte count which is often used for the index of the influence of radiation exposure was determined and the inhibitory rate of leukopenia, I, was calculated by the following equation:

$$I = \left[ \frac{(\text{Leukocyte count of non-irradiated group}) - (\text{Leukocyte count of the administered group of the extract})}{(\text{Leukocyte count on non-irradiated group}) - (\text{Leukocyte count of the control group})} \right] \times 100 \, (\%)$$

$(n = 10)$

The control group was administered 10 ml/kg of distilled water instead of the extract.

The results are shown in Table 8 revealing an inhibitory effect of the substance of the present invention against leukopenia caused by radiation exposure. The results also indicate a possibility of the extract for the application to the prevention and treatment of the decline of vital functions due to the radiation exposure and the extract will become a very important substance for terrestrial livings including human being under the progress of radioactive contamination.

TABLE 8

| Resource of extract of malt residue | Inhibitory rate of leukopenia, I |
| --- | --- |
| Barley | ++ |
| Wheat | + |
| Naked barley | + |
| Rye | ++ |
| Oats | + |

The inhibitory rates, I, in the above Table 8 are classified by the following grades:

| | | |
| --- | --- | --- |
| —; | $0 \leq I <$ | $10(\%)$ |
| +; | $10(\%) \leq I <$ | $20(\%)$ |
| ++: | $20(\%) \leq I \leq$ | $100(\%)$ |

EXAMPLE 11

One thousand mg of the dried extracts obtained by Example 1 or 2 was dissolved in 20 ml of distilled water and orally administered by gavage at a rate of 1,000 mg/kg to 16 weeks old male spontaneously hypertensive rats (hereinafter abbreviated as SHR rats). After three hours, the blood pressure were determined to examine the hypotensive effect. The blood pressure was determined by Rat Tail Manometer-Touchmeter System KN-209 (Natsume Seisakusho Co., Ltd.) after keeping the SHR rats in a pre-heat box (Natsume Seisakusho Co., Ltd.) at 45° C. for two minutes. The control group was administered 20 ml/kg or distilled water instead of the extract. The results are shown in Table 9, revealing an excellent hypotensive effect of the substance in SHR rats. The results also indicate the possibility of the application of extract for the prevention and treatment of hypertensions.

TABLE 9

| Resource of extract of malt residue | Hypotensive rate, L |
| --- | --- |
| Barley | ++ |
| Wheat | + |
| Naked barley | + |
| Rye | ++ |
| Oats | ++ |

The hypotensive rates, L, in the above Table 9 are classified by the following grades:

| | | |
| --- | --- | --- |
| —; | $0 \leq L <$ | $10(\%)$ |
| +; | $10(\%) \leq L <$ | $20(\%)$ |
| ++; | $20(\%) \leq L \leq$ | $100(\%)$ |

The hypotensive rate, L, calculated by the following equation.

$$L = \left[ 1 - \frac{\text{Blood pressure three hours after the administration of the extract}}{\text{Blood pressure after three hours in the control group}} \right] \times 100 \, (\%)$$

$(n = 6)$

EXAMPLE 12

Sixty mg/kg of streptozocin was intravenously administered once to 10 weeks old male Wistar rats according to the method of Hatanaka et al. Five days after the administration, urine sugar and blood sugar were determined. Rats confirmed with the diabetes and hyperglycemia were enrolled the test. One thousand mg of the dried extract obtained by Example 1 of 2 was dissolved in 20 ml of distilled water and administered orally by gavage at a rate of 1,000 mg/kg to the enrolled rats. After three hours, the blood was drawn and blood sugar was determined by RABA Super. The control group was administered 20 ml/kg of distilled water instead of the extract. The results are shown in Table 10, revealing an excellent hypoglycemic effect of the extract of the present invention in streptozocin induced diabetes model rats. The results also indicate that the extract can be applied for the prevention and treatment of diabetes.

TABLE 10

| Resource of extract of malt residue | Hypoglycemic rate, L |
| --- | --- |
| Barley | ++ |
| Wheat | + |
| Naked barley | + |
| Rye | + |
| Oats | ++ |

The hypoglycemic rates, L, in the above Table 10 are classified by the following grades:

| | | |
| --- | --- | --- |
| −; | $0 \leq L <$ | $10(\%)$ |
| +; | $10(\%) \leq L <$ | $15(\%)$ |
| ++; | $15(\%) \leq L \leq$ | $100(\%)$ |

The hypoglycemic rate, L, calculated by the following equation.

$$L = \left[ 1 - \frac{\text{Blood sugar three hours after the administration of the substance}}{\text{Blood sugar after three hours in the control group}} \right] \times 100\ (\%)$$

$(n = 6)$

EXAMPLE 13

This Example exemplifies a pharmaceutical preparation of the extract of the present invention.

One kg of the spray dried extract obtained by Example 1 or 2 was mixed with one kg of lactose, 500 g of hydroxypropyl-cellulose and 20 g of calcium stearate. The mixture was prepared tablets having a diameter of 8 mm and weighing 252 mg/tablet by rotary tabletting machine (HT-9 type).

The following Examples 14-19 illustrate the practical applications of the extract of the present invention to foods and drinks.

EXAMPLE 14

Dried extract obtained by Example 1 or 2 was sieved and sterilized. Three g of the sterilized product and 58 g of commercial powdered drink were mixed in mortar for 30 minutes to give a powdered drink containing the extract of the present invention.

EXAMPLE 15

Three parts of the dried extract obtained by Example 1 or 2 was added to a mixture of 100 parts of wheat flour, 1.4 parts of salt, 0.14 part of brine (dried weight, seasoning for cooking), 32 parts of water, and a small amount of starch and natural rubber. The obtained mixture was kneaded, rolled, formed to noodles, steam heated, cut, molded, fried and cooled to give a fried noodles.

EXAMPLE 16

One hundred parts of a commercial orange juice and two parts of the dried extract obtained by Example 1 or 2 were thoroughly mixed to give an orange drink containing the extract of the present invention.

EXAMPLE 17

Five parts of the dried extract obtained by Example 1 or 2 and 100 parts of a commercial milk were mixed thoroughly to give a milk containing the extract or the present invention.

EXAMPLE 18

One part of the dr led extract obtained by Example 1 or 2 and 100 parts of commercial mineral water were mixed thoroughly to give a mineral water containing the extract of the present invention.

EXAMPLE 19

Ten parts of the dried extract obtained by Example 1 or 2 and 100 parts of a commercial hot cake mix powder were mixed thoroughly to give a hot cake mix (powder form) containing the extract of the present invention. The obtained product can be used to prepare delicious hot cakes similar to a conventional hot cake mix (powder form).

As clearly described, the present invention can provides a physiologically useful substance for maintaining the human health from residue of saccharification of malt, which has been worthless and improved value of the malt residue, a by-product of saccharification malt. Furthermore, the obtained physiologically active extract can be used for the raw materials of functional foods and drinks or an effective ingredient of medicines.

What is claimed is:

1. A pharmaceutical composition comprised of
   1) an extract which is derived from malt residue and prepared by saccharification of malt, filtration of the saccharified mixture, extraction of the filtered residue with water or an aqueous solvent and removal of a low molecular weight fraction from the extract and wherein said extract has the following properties:
      (i) Molecular weight of from $19.8 \times 10^4$ to $22.1 \times 10^4$ daltons as determined by the GPC-LALLS method,
      (ii) Infrared absorption spectra at 3,600–3,200 $cm^{-1}$ and 1,700–1,6000 $cm^{-1}$,
      (iii) Proton nuclear magnetic resonance spectra having peaks at 0.5–6.0 ppm and 6.0–8.5 ppm,
      (iv) Ultraviolet absorption spectra at 200–250 nm and 250–350 nm,
      (v) Positive to phenol sulfuric acid color reaction, and
      (vi) Positive to copper-Folin color reaction, and 2) a pharmaceutically acceptable carrier or diluent.

2. A pharmaceutical composition comprised of
1) an extract derived from malt residue having the following properties:
   (i) said extract is free of fractions having a molecular weight as determined by the GPC-LALLS method of below 2,000 daltons,
   (ii) Infrared absorption spectra at 3,600–3,200 $cm^{-1}$,
   (iii) Proton nuclear magnetic resonance spectra having peaks at 0.5–6.0 ppm and 6.0–8.5 ppm,
   (iv) Ultraviolet absorption spectra at 200–250 nm and 250–350 nm,
   (v) Positive to phenol sulfuric acid color reaction,
   (vi) Positive to copper-Folin color reaction, and
2) a pharmaceutically acceptable carrier or diluent.

* * * * *